US00PP18345P2

(12) United States Plant Patent

Guillou et al.

(10) Patent No.: US PP18,345 P2

(45) Date of Patent: Dec. 25, 2007

(54) *GERANIUM* PLANT NAMED 'GUIGLORIA'

(50) Latin Name: *Pelargonium peltatum*
Varietal Denomination: Guigloria

(75) Inventors: Bernard Guillou, Saint-Malo (FR); Maurice Guillou, Saint-Malo (FR)

(73) Assignee: Fides B.V., De Lier (NL)

( * ) Notice: Subject to any disclaimer, the term of this patent is extended or adjusted under 35 U.S.C. 154(b) by 0 days.

(21) Appl. No.: 11/494,122

(22) Filed: Jul. 27, 2006

(51) Int. Cl.
*A01H 5/00* (2006.01)

(52) U.S. Cl. ..... Plt./332

(58) Field of Classification Search ..... Plt./332
See application file for complete search history.

*Primary Examiner*—Kent L. Bell
(74) *Attorney, Agent, or Firm*—C. A. Whealy

(57) ABSTRACT

A new and distinct cultivar of Ivy *Geranium* plant named 'Guigloria', characterized by its outwardly spreading and trailing plant habit; freely basal branching habit; freely flowering habit; double white-colored flowers with red purple-colored linear markings; and good garden performance.

1 Drawing Sheet

Botanical designation: *Pelargonium peltatum.*
Cultivar denomination: 'Guigloria'.

BACKGROUND OF THE INVENTION

The present invention relates to a new and distinct cultivar of Ivy *Geranium*, botanically known as *Pelargonium peltatum,* and hereinafter referred to by the name 'Guigloria'.

The new Ivy *Geranium* is a product of a planned breeding program conducted by the Inventors in Saint Malo, France. The objective of the breeding program is to create new freely-branching and freely-flowering Ivy *Geranium* cultivars with attractive foliage and flower coloration.

The new Ivy *Geranium* originated from a cross-pollination made by the Inventors in Saint Malo, France of two unnamed selections of *Pelargonium peltatum,* not patented. The cultivar Guigloria was discovered and selected by the Inventors as a flowering plant from within the progeny of the stated cross-pollination in a controlled environment in Saint Malo, France.

Asexual reproduction of the new Ivy *Geranium* by vegetative terminal cuttings in a controlled environment in De Lier, The Netherlands, has shown that the unique features of this new Ivy *Geranium* are stable and reproduced true to type in successive generations.

SUMMARY OF THE INVENTION

The cultivar Guigloria has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Guigloria'. These characteristics in combination distinguish 'Guigloria' as a new and distinct cultivar of Ivy *Geranium:*

1. Outwardly spreading and trailing plant habit.
2. Freely basal branching habit.
3. Freely flowering habit.

4. Double white-colored flowers with red purple-colored linear markings.
5. Good garden performance.

Plants of the new Ivy *Geranium* differ primarily from plants of the parent selections in plant size and flower color.

Plants of the new Ivy *Geranium* can be compared to plants of the *Pelargonium peltatum* cultivar Meritropical, disclosed in U.S. Plant Pat. No. 11,115. In side-by-side comparisons conducted in De Lier, The Netherlands, plants of the new Ivy *Geranium* differed from plants of the cultivar Meritropical in the following characteristics:

1. Plants of the new Ivy *Geranium* were more vigorous than plants of the cultivar Meritropical.
2. Plants of the new Ivy *Geranium* and the cultivar Meritropical differed in flower color.
3. Plants of the new Ivy *Geranium* were more weather tolerant than plants of the cultivar Meritropical.

BRIEF DESCRIPTION OF THE PHOTOGRAPH

The accompanying colored photograph illustrates the overall appearance of the new Ivy *Geranium*, showing the colors as true as it is reasonably possible to obtain in colored reproductions of this type. Colors in the photograph may differ slightly from the color values cited in the detailed botanical description which accurately describe the colors of the new Ivy *Geranium*. The photograph comprises a side perspective view of a typical flowering plant of 'Guigloria' grown in a hanging basket container.

DETAILED BOTANICAL DESCRIPTION

The photographs and following observations, measurements and values describe plants grown in De Lier, The Netherlands in a glass-covered greenhouse during the winter and early spring and under conditions which closely approximate commercial production. During the production of the plants, day temperatures ranged from 14° C. to 20° C., night temperatures ranged from 14° C. to 18° C. and light levels ranged from 10,000 lux to 50,000 lux. Plants were about four months old when the photographs and the description were taken. In the detailed description, color references are made to The Royal Horticultural Society Colour Chart, 1995 Edition, except where general terms of ordinary dictionary significance are used.

Botanical classification: *Pelargonium peltatum* cultivar Guigloria.

Parentage:

*Female, or seed, parent.*—Unnamed selection of *Pelargonium peltatum,* not patented.

*Male or pollen parent.*—Unnamed selection of *Pelargonium peltatum,* not patented.

Propagation:

*Type.*—By vegetative terminal cuttings.

*Time to initiate roots, summer.*—About 10 days at temperatures of 20° C.

*Time to initiate roots, winter.*—About 10 days at temperatures of 20° C.

*Time to produce a rooted young plant, summer.*—About two to three weeks at temperatures of 20° C.

*Time to produce a rooted young plant, winter.*—About two to four weeks at temperatures of 20° C.

*Root description.*—Fine, fibrous; white in color.

*Rooting habit.*—Freely branching, moderately dense.

Plant description:

*General appearance.*—Outwardly spreading and trailing plant habit; uniformly mounded; densely foliated.

*Growth and branching habit.*—Moderately vigorous to vigorous growth habit. Freely basal branching habit with about ten lateral branches per plant.

*Plant height, to top of umbels.*—About 15 cm to 25 cm.

*Plant width.*—About 12 cm to 20 cm.

*Lateral branches.*—Length: About 5 cm to 25 cm. Diameter: About 3 mm to 6 mm. Internode length: About 3 cm to 6 cm. Texture: Pubescent. Strength: Moderately strong. Color: 144C.

Foliage description:

*Arrangement.*—Alternate; simple.

*Length.*—About 5 cm to 8 cm.

*Width.*—About 5 cm to 10 cm.

*Shape.*—Orbicular.

*Apex.*—Acute.

*Base.*—Cordate; open.

*Margin.*—Crenate; slightly undulate.

*Venation pattern.*—Palmate.

*Texture, upper surface.*—Slightly pubescent.

*Texture, lower surface.*—Smooth, glabrous.

*Color.*—Developing foliage, upper surface: 143A. Developing foliage, lower surface: 143C. Fully developed, upper surface: 137A; venation, 143A. Fully developed, lower surface: 137D; venation, 143C. Zonation pattern: Intensity: Moderate. Color: 177A. Petiole: Length: About 3.5 cm to 7 cm. Diameter: About 3 mm. Texture, upper and lower surfaces: Smooth, glabrous. Color, upper and lower surfaces: 143C.

Flower description:

*Flower arrangement.*—Double rotate flowers arranged in rounded hemispherical umbels arising from apical leaf axils. Umbels displayed above the foliage on strong peduncles. Flowers face upright to outward; flowers mostly flat. Flowers not persistent. Flowers not fragrant.

*Quantity of flowers.*—Freely flowering habit; about 4 to 30 flower buds and open flowers per umbel.

*Flowering season.*—Year-round under greenhouse conditions. In the garden in De Lier, The Netherlands, flowering is continuous from spring until frost in autumn.

*Flower longevity.*—Individual flowers last about 2 to 14 days on the plant.

*Umbel height.*—About 4 cm to 7 cm.

*Umbel diameter.*—About 4 cm to 9 cm.

*Flower diameter.*—About 2 cm to 2.5 cm.

*Flower depth* (*height*).—About 1.9 cm.

*Flower buds.*—Length: About 6 mm to 8 mm. Diameter: About 4 mm to 6 mm. Shape: Broadly elliptic. Color: 143C.

*Petals.*—Quantity per flower: About 10 to 30. Length: About 1.8 cm to 2.8 cm. Width: About 2 mm to 9 mm. Shape: Lanceolate to ovate. Apex: Rounded. Base: Attenuate. Margin: Entire. Texture, upper and lower surfaces: Smooth, glabrous; velvety. Color: When opening, upper surface: 157D. When opening, lower surface: 158C. Fully opened, upper surface: 155D: linear markings, close to 67B to 67A. Fully opened, lower surface: 155D.

*Petaloids.*—Quantity per flower: About 2 to 25. Length: About 1 mm to 2 cm. Width: About 1 mm to 9 mm. Shape: Narrowly obovate to irregularly oblanceolate. Apex: Rounded. Base: Attenuate. Margin: Entire. Texture, upper and lower surfaces: Smooth, glabrous; velvety. Color: When opening and fully opened, upper surface: 157D; linear markings, 67B to 67A. When opening and fully opened, lower surface: 157D.

*Sepals.*—Quantity per flower: Five, arranged in a single whorl. Length: About 1 cm to 1.2 cm. Width: About 2 mm to 3 mm. Shape: Lanceolate. Apex: Acute. Base: Cuneate. Margin: Entire. Texture, upper and lower surfaces: Densely pubescent. Color, upper and lower surfaces: 144A.

*Peduncle* (*umbel stem*).—Length: About 8 cm to 15 cm. Diameter: About 3 mm to 4 mm. Strength: Moderately strong. Angle: Erect to about 30° from vertical. Texture: Pubescent. Color: 144A.

*Pedicel* (*individual flower stem*).—Length: About 5 mm to 2.5 cm. Diameter: About 2 mm to 3 mm. Strength: Moderately strong. Angle: Erect to about 110° from vertical. Texture: Pubescent. Color: 144B.

*Reproductive organs.*—Androecium: Stamen quantity per flower: None to about eight. Filament length: About 1 cm. Filament color: 155A. Anther length: About 3 mm. Anther shape: Oblong. Anther color: 183A to 183B. Pollen amount: Moderate. Pollen color: 172B. Gynoecium: Pistil quantity per flower: One. Pistil length: About 5 mm to 1 cm. Stigma shape: Tapering; reflexed. Stigma color: 187B. Style length: About 5 mm to 10 mm. Style color: 160D. Ovary color: 141C.

*Seed.*—Seed development has not been observed.

Disease/pest resistance: Plants of the new Ivy *Geranium* have not been observed to be resistant to pathogens and pests common to Ivy *Geraniums*.

Garden performance: Plants of the new Ivy *Geranium* have been observed to tolerate rain, wind, and temperatures ranging from about 0° C. to about 45° C. and have demonstrated good garden performance.

It is claimed:

1. A new and distinct Ivy *Geranium* plant named 'Guigloria' as illustrated and described.

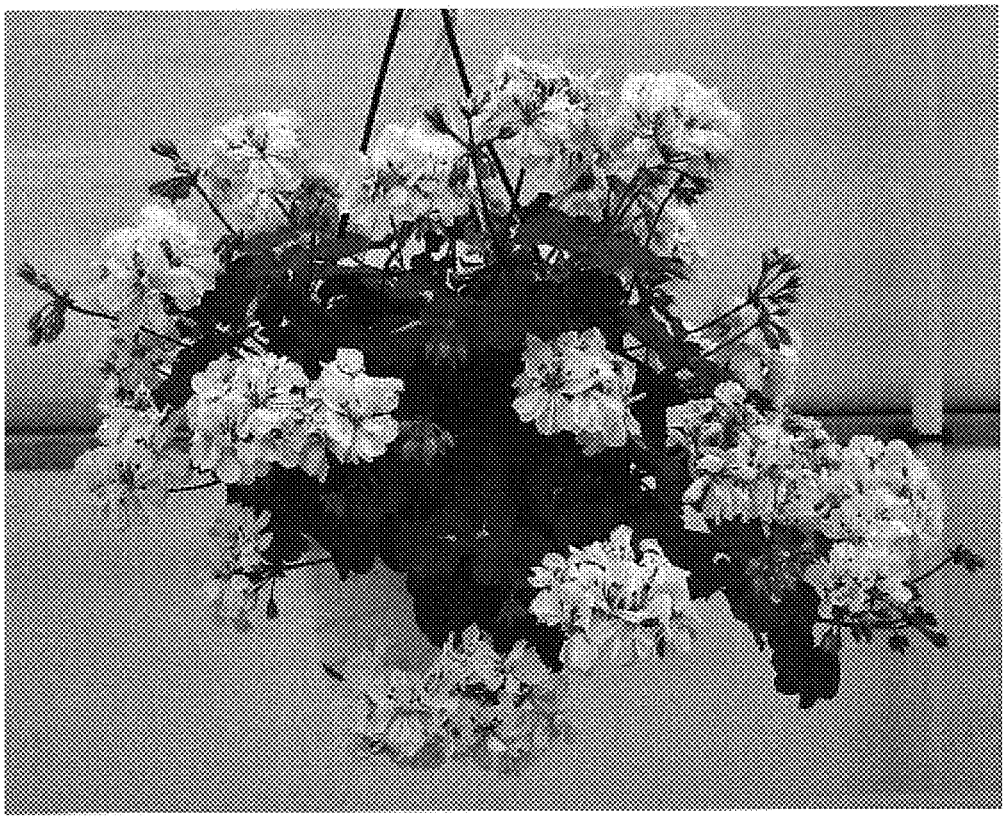

* * * * *